US008141552B2

(12) United States Patent
Daviet et al.

(10) Patent No.: US 8,141,552 B2
(45) Date of Patent: Mar. 27, 2012

(54) RESPIRATORY ANAESTHESIA APPARATUS WITH DEVICE FOR MEASURING THE XENON CONCENTRATION

(75) Inventors: Christian Daviet, Paris (FR); Richard Blandin, Paris (FR); Noureddine Kissi, Meudon la Foret (FR)

(73) Assignee: L'Air Liquide Societe Anonyme pour l'Etude Et l'Exploitation des Procedes Georges Claude, Paris (FR)

( * ) Notice: Subject to any disclaimer, the term of this patent is extended or adjusted under 35 U.S.C. 154(b) by 804 days.

(21) Appl. No.: 12/097,216

(22) PCT Filed: Dec. 11, 2006

(86) PCT No.: PCT/FR2006/051326
§ 371 (c)(1),
(2), (4) Date: Oct. 1, 2008

(87) PCT Pub. No.: WO2007/068849
PCT Pub. Date: Jun. 21, 2007

(65) Prior Publication Data
US 2009/0090359 A1    Apr. 9, 2009

(30) Foreign Application Priority Data

Dec. 14, 2005  (FR) .................................... 05 53862

(51) Int. Cl.
*A61M 11/00*    (2006.01)
(52) U.S. Cl. .............................. 128/203.12; 128/204.22
(58) Field of Classification Search ............. 128/203.12, 128/203.16, 203.17, 203.26, 204.18, 204.21, 128/204.22, 203.27, 204.17
See application file for complete search history.

(56) References Cited

U.S. PATENT DOCUMENTS

| 3,913,379 A | 10/1975 | Rusz et al. |
| 4,903,693 A | 2/1990 | Yasue et al. |

(Continued)

FOREIGN PATENT DOCUMENTS

DE    296 13 243    10/1996

(Continued)

OTHER PUBLICATIONS

Written Opinion for related PCT/FR2006/051326, Aug. 6, 2007.

(Continued)

*Primary Examiner* — Steven Douglas
(74) *Attorney, Agent, or Firm* — Allen E. White

(57) ABSTRACT

Apparatus for respiratory anaesthesia of a patient by administration of a gas containing gaseous xenon, with a main gas circuit which is open or closed and has an inhalation branch and an exhalation branch, means for supply of gaseous xenon to the inhalation branch of the main circuit, and means for determining the xenon concentration. The means for determining the xenon concentration comprise at least one hot-wire sensor having at least one electrically conducting wire in direct contact with the gaseous flow containing the xenon, calculating means that cooperate with the hot-wire sensor(s) in order to determine the xenon concentration (Xe %) in the flow, means for generating an electrical current in order to generate a current in at least one hot wire, and means for voltage measurement that can measure at least one voltage value at the terminal of at least one hot wire or at least one resistance arranged in series with at least one hot wire. The calculating means cooperate with the voltage measurement means in such a way as to determine the xenon concentration (Xe %).

20 Claims, 10 Drawing Sheets

U.S. PATENT DOCUMENTS

| | | | |
|---|---|---|---|
| 4,905,685 A | 3/1990 | Olsson et al. | |
| 5,230,331 A * | 7/1993 | Rusz et al. | 128/205.23 |
| 6,305,212 B1 | 10/2001 | Drzewiecki | |
| 6,349,722 B1 * | 2/2002 | Gradon et al. | 128/203.17 |
| 6,945,123 B1 | 9/2005 | Kuehl et al. | |
| 2001/0022181 A1 | 9/2001 | Masson et al. | |
| 2008/0029091 A1 | 2/2008 | Müllner | |

FOREIGN PATENT DOCUMENTS

| | | |
|---|---|---|
| DE | 297 06 003 | 8/1997 |
| DE | 197 45 954 | 4/1999 |
| DE | 10 2004 015406 | 10/2005 |
| EP | 0 523 315 | 1/1993 |
| EP | 0 723 147 | 7/1996 |
| EP | 0 983 771 | 3/2000 |
| EP | 1 120 126 | 8/2001 |
| EP | 1 318 797 | 6/2003 |
| EP | 1 499 377 | 1/2005 |
| FR | 2 894 486 | 6/2007 |
| FR | 2 894 487 | 6/2007 |
| WO | WO 92 03724 | 3/1992 |
| WO | WO 00 50890 | 8/2000 |
| WO | WO03/091718 | 11/2003 |
| WO | WO 03 092776 | 11/2003 |
| WO | WO 2005 022122 | 3/2005 |
| WO | WO 2007 068849 | 6/2007 |

OTHER PUBLICATIONS

French Search Report for related FR 2 894 486, Sep. 14, 2006.
French Search Report for related FR 2 894 487, Sep. 18, 2006.
International Search Report for PCT/FR2006/051326, (2006).

* cited by examiner

RESPIRATORY ANAESTHESIA APPARATUS WITH DEVICE FOR MEASURING THE XENON CONCENTRATION

This application is a §371 of International PCT Application PCT/FR2006/051326, filed Dec. 11, 2006.

The present invention relates to an anesthesia apparatus using xenon provided with a device for measuring the xenon concentration.

BACKGROUND

1. Field of the Invention

The invention relates, in other words to a device for measuring the xenon concentration designed to be integrated in anesthesia apparatus (integrated system), the respiratory anesthesia apparatus comprising a main circuit for leading a gas flow for administering to the patient an anaesthetic gas mixture containing xenon, and a respiratory system for ventilating the anesthetized patient.

2. Related Art

Many respiratory anesthesia apparatuses are known that can be used for producing anesthesia of a patient who has to undergo a surgical operation or the like, by administering to him or her a conventional anaesthetic gas mixture by inhalation, composed of $N_2O$, halogenated agents (for example Sevoflurane, Isoflurane, Desflurane). In this connection, reference may be made for example to documents EP-A-983 771 and EPA-A-1 120 126.

Among the gas mixtures that may be used, those based on xenon will be increasingly used with indications particularly suited to delicate patients (elderly patients, long operations, cardiac surgery, neurosurgery, etc.) on account of, in particular, the virtually zero influence on blood pressure during anesthesia and the absence of secondary and harmful effects from xenon.

However, anesthesia carried out with xenon requires xenon concentrations in the gas flow administered to the patient to be followed or monitored, that is to say it requires the ability to determine in real time the xenon concentration in the anesthetic flow.

To this end, reference may be made for example to documents EP-A-1 499 377, EP-A-1 318 797 or EP-A 523 315.

At the present time, a mass spectrometer or chromatograph is conventionally used for measuring a xenon concentration in such a gas mixture.

Now, these techniques have disadvantages regarding cost and especially the difficulty of implementing them, since their integration into existing anesthesia apparatuses requires very considerable development and adaptation efforts.

SUMMARY OF THE INVENTION

The invention claims to solve all or part of the problems of the abovementioned prior art, and in particular the invention aims to provide a respiratory anesthesia apparatus with xenon making it possible to determine with precision the xenon concentration delivered to the patient during gas anesthesia so as to guarantee effective anesthesia and increased safety for the patient, while having a simple architecture and modest cost.

The present invention relates to a means of following or monitoring gaseous xenon concentrations in an anesthesia gas mixture based on xenon that contains a variable quantity of one or more of the following components: oxygen, nitrogen, nitrous oxide, carbon dioxide, halogenated compounds of the isoflurane, enflurane, desflurane, sevoflurane or halothane type, ethanol and possibly traces or small quantities of one or more minor components. The present invention therefore provides an apparatus for respiratory anesthesia of a patient by administration of a gas containing gaseous xenon.

BRIEF DESCRIPTION OF THE FIGURES

The invention will be better understood from the following description made with reference to the appended drawings, among which.

DETAILED DESCRIPTION OF THE INVENTION

Figure 1:
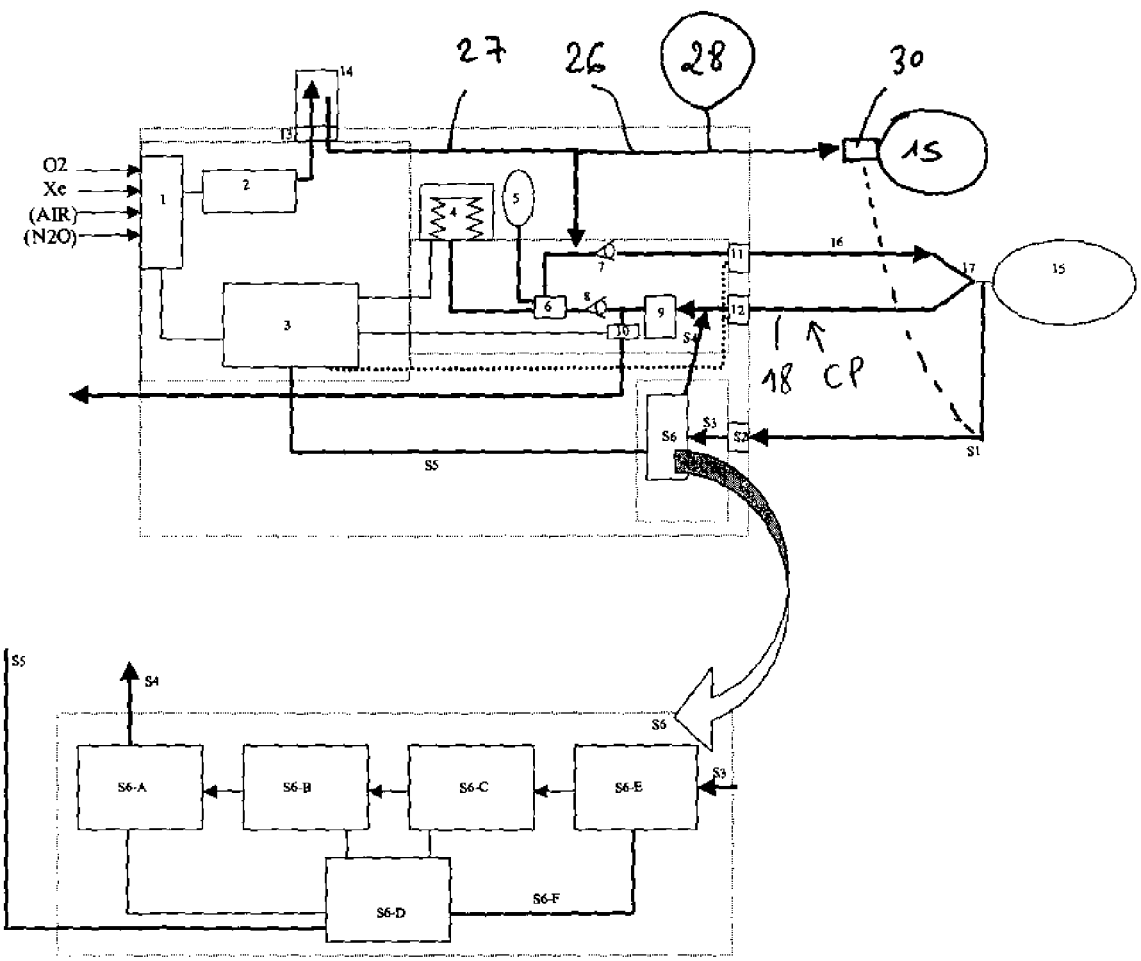
FIG. 1 shows a first embodiment of an apparatus according to the invention that may be used for anesthesia under xenon with the possible use of halogenated compounds and with a hot wire or wires placed in the diverted gas flow.

In other words, the invention concerns the particular problem of following or monitoring gaseous xenon concentrations in an anesthesia gas mixture based on xenon containing, in addition, a variable quantity, that is to say from 0 to 100% by volume, of one or more of the following main components: oxygen, ($O_2$) nitrogen ($N_2$), nitrous oxide ($N_2O$), carbon dioxide ($CO_2$), halogenated compounds of the isofluorane, enflurane, desflurane, sevoflurane or halothane type, ethanol, and possibly traces or small quantities (<1%) of one or more of the following minor components: acetone, methane, carbon monoxide (CO), argon, helium etc.

In other words, the invention aims to provide special means making it possible to determine efficiently, easily and with sufficient precision the xenon content in a flow of anaesthetic gas, it being possible for said means to be incorporated in a new apparatus or an existing apparatus, that is to say to constitute an integrated monitoring system, or one that can be associated with existing apparatuses, that is to say forming an external self-contained monitoring system.

To this end, the invention provides an apparatus for respiratory anesthesia of a patient by administration of a gas containing gaseous xenon comprising a main gas circuit in an open or closed circuit having an inhalation branch for leading a gas mixture containing xenon to the patient and an exhalation branch for conveying the gas mixture containing xenon exhaled by the patient, means for supplying gaseous xenon connected to the main circuit for supplying the inhalation branch of the main circuit with a gas containing xenon, means for determining the xenon concentration in order to determine the gaseous xenon content in at least part of the main circuit.

The apparatus according to the invention is characterized in that said means for determining the xenon concentration comprise:

at least one hot-wire(s) sensor having at least one wire made of electrically conducting material, preferably of metal, in direct contact with at least part of the gas flow containing xenon, and calculating means cooperating with the hot-wire(s) sensor so as to determine the xenon concentration (Xe %) in said gas flow, means for generating an electric current, preferably adjustable, capable of and designed for generating an electric current, continuous or not, in the hot wire or hot wires of said at least one adjustable hot-wire(s) sensor and, means for measuring the voltage capable of measuring at least one voltage value at the terminals of at least one hot wire or a resistance placed in series with at least one hot wire when said at least one hot wire is in contact with said gas flow and is traversed by an electric current of intensity (I), and in that the calculating means cooperate with the means for measuring voltage so as to determine, from the voltage measurement carried out by said voltage measuring means, the xenon concentration (Xe %) in said flow.

Advantageously, the apparatus of the invention may include one or more of the following characteristics:

it includes adjustable means for generating a current capable of and designed for generating an electric current in the hot wire or in each of the hot wires of said at least one hot-wire sensor, said means for generating a current being designed for, and being capable of controlling the intensity of the electric current passing through the hot wire or wires of said at least one hot-wire sensor, so that, whatever the composition of the gas passing over said at least one hot-wire sensor(s), the intensity of the current passing through the hot wire or wires is kept substantially constant and/or the temperature of the hot wire or wires of said at least one hot-wire(s) sensor is kept substantially constant. In other words, the means for generating a current enable the intensity of the current passing through the wire to be controlled, whatever the composition of the gas, so that:

either the intensity I is kept constant. In this case, variations in xenon concentrations around the wire bring about a temperature variation that leads to a variation in the resistance R of the wire. Since the current I is kept constant or approximately constant in the hot wire of the hot-wire(s) sensor, the voltage V will be measured (equal to R×I) at the terminals of the hot wire of hot-wire(s) sensor in order to deduce the Xe % concentration from the linear curve corresponding to the flow rate D, measured or known, as detailed hereinafter in the description, or the temperature of the wire is kept constant. In this case, variations of the current (I) are adjusted so as to keep the temperature of the hot wire constant or approximately constant, and in this way to compensate for the effect of xenon concentration variations around the wire. If the Xe concentration increases, this increase will have the tendency to bring about an increase in the wire temperature, and the means for generating current will then react so as to bring about a reduction in the current (I) passing through the wire, since such a reduction will have the tendency to reduce the wire temperature according to Joule's law, and in this way to bring about a convergence toward an equilibrium enabling the temperature to remain constant. On the other hand, if the Xe concentration falls, this fall will have the tendency to bring about a reduction in the temperature of the wire, and the means for generating a current will then react to bring about an increase in the current I passing through the wire, since this increase will have the tendency to cause the temperature of the wire to increase and thus to bring about a convergence toward an equilibrium enabling the temperature to remain constant. A choice will then be made to measure the voltage V at the terminals of a resistance Rs inserted in series with the hot wire of the hot-wire(s) sensor, V being equal to Rs×I, so as to deduce therefrom the Xe % concentration from the linear curve corresponding to the flow rate D, measured or known, as detailed hereinafter in the description, the calculating means use at least one value of the voltage (V) transmitted by the voltage measuring means and at least one value of the flow rate of anaesthetic gas containing xenon in order to determine the xenon concentration (Xe %) in said gas flow, the hot-wire(s) sensor is arranged on a bypass line communicating fluidically with the main circuit. The bypass line is connected to the main circuit on the inhalation branch and/or on the exhalation branch and/or in a site located in the immediate vicinity of the patient's mouth, preferably in the region of a connecting site between the inhalation branch and the exhalation branch of said main circuit, for example in the region of a connecting Y-piece or a bacteriological filter arranged on the main circuit, that is to say at the junction of the inhalation and exhalation branches of the main circuit. This type of architecture using a bypass line is known under the name "side-stream type".

means for controlling the gas flow, in particular a suction pump, are arranged on the bypass line so as to obtain a known anaesthetic gas flow rate, preferably a constant and/or stable gas flow rate. A constant and/or stable gas flow rate is understood to mean that the flow rate varies at most by a few % with respect to its mean value, for example by approximately 3% maximum, that is to say the amplitude of the flow rate variation, plus or minus, with respect to said mean value of the flow rate has a negligible impact on the various sensors and measuring means used, the means for controlling the gas flow rate make it possible to control the flow rate of gas containing xenon so as to provide a desired, preferably constant and/or stable flow rate of the gas conveyed by the bypass line and put into contact with at least one hot wire, the means for controlling the gas flow rate comprise a pump for aspirating gas, and the suction pump is preferably associated with electronics for controlling said pump, that is to say electronics that control the suction pump in order to draw off from the main circuit a desired, precise and stable flow over time of gas containing xenon to be analyzed. An example of such means associating a suction pump and electronics for controlling the pump are to be found in the Andros BGA4800 gas analyzer, the calculating means are incorporated in a gas analyzer module connected to the main circuit.

one or more hot-wire(s) sensors are arranged directly on the main circuit, for example on the inhalation branch and/or the exhalation branch and/or at the junction between the inhalation and exhalation branches, the apparatus having means for measuring the inhalation flow rate and/or the exhalation flow rate and/or the main flow rate at the junction between the inhalation and exhalation branches of the gas flow circulating in the main circuit, these means for measuring flow rate preferably comprising an inhalation flow rate sensor and an exhalation flow rate sensor, arranged respectively on the inhalation and exhalation branches of the main circuit (also called the "patient circuit"), in order to measure the inhalation and exhalation flow rates in said branches and to transmit the measurement signals obtained in this way to control means so as to determine, in combination with the voltage measurements transmitted by the voltage measuring means associated with said one or more hot-wire sensors arranged directly on the main circuit, the xenon concentration in the inhalation branch and/or the exhalation branch and/or at the junction between the inhalation and exhalation branches. This architecture not using a bypass line is known under the name "main-stream type", the calculating means are incorporated in the module for controlling the ventilator.

the hot-wire(s) sensor has one or more platinum wires, the hot-wire(s) sensor has several wires having different orientations relative to the gas flow, preferably two hot wires, the calculating means are incorporated in or form means for controlling the apparatus, the calculating means are incorporated in or form means for controlling the gas analyzer module, the calculating means include at least one electronic card and/or a computer program for performing all or part of the calculations enabling the xenon concentration in the anaesthetic gas to be determined, the apparatus includes means for measuring a concentration of at least one supplementary gas distinct from xenon such as $O_2$, $CO_2$ and $N_2O$, halogenated gases or ethanol, the calculating means cooperating with the means for measuring a concentration of at least one supplementary gas in order to determine at least one of the following xenon concentrations: instantaneous, mean, inhaled, exhaled, means for measuring the concentration of at least one supplementary gas comprising means of the infrared type (for supplementary gases such as $CO_2$, $N_2O$, halogenated gases or ethanol) and/or of the paramagnetic or chemical type (for supplementary gases such as $O_2$), the apparatus includes means for measuring the relative humidity of the analyzed gas flow, the calculating means cooperating with the means for measuring the relative humidity in order to improve the calculating precision of at least one of the following xenon concentrations: instantaneous, mean, inhaled, exhaled, the apparatus includes means for measuring the temperature of the analyzed gas, the calculating means cooperating with these means for measuring the temperature in order to improve the calculating precision of at least one of the following xenon concentrations: instantaneous, mean, inhaled, exhaled, the apparatus additionally includes an auxiliary gas circuit having an auxiliary inhalation branch enabling a respiratory gas containing xenon to be led to the patient by means of a manual insufflator, the means for determining the xenon concentration being designed and adapted so as to that they can be connected to said auxiliary gas circuit in order to determine therein the xenon content when the gas containing xenon is administered to the patient via said auxiliary gas circuit, in particular in the case where the main circuit ceases to operate or malfunctions, the calculating means use voltage values (V) and flow rate values (D) for determining a xenon concentration (Xe %) in the gas flow from one or more linear curves memorized in the memory means of the apparatus, preferably one of the straight lines of the type:

$a \times [Xe]+b=V$ where V is the voltage, [Xe] is the xenon concentration and a and b are positive or negative coefficients corresponding to a given flow rate D, the curve or curves, for as many values of the flow rate (Dn) that are desired or necessary, are calibrated (with a flow rate established at a value (Dn) of gas of which the xenon content is known, namely pure xenon and/or pure $O_2$ and/or pure air) before being memorized and/or periodically and automatically updated during the use of the apparatus, the bypass line is connected to the main circuit in a site localized in the immediate vicinity of the patient's mouth, even more preferably in the region of a connecting site between the inhalation branch and the exhalation branch of said main circuit, for example in the region of a connecting Y-piece or a bacteriological filter arranged on the main circuit.

The invention also relates to a method for anesthetizing a patient in which an inhalation gas containing xenon is administered into the upper airways of the patient so as to produce gas anesthesia of said patient, and the xenon content is determined of the gas administered to the patient by means of an anesthesia apparatus according to the invention.

The present invention is therefore based on the use of one or more hot-wire(s) sensor(s) in order to determine, in real time, the instantaneous and/or mean concentration of xenon present in the anaesthetic gas.

The principle for measuring the flow rate of an anaesthetic gas by means of hot wire(s) sensor is as follows.

In a general manner, when a given electric current (I) is passed through a metal wire (F) (a platinum wire is conventionally used) with a given cross section (S) placed in a flow of anaesthetic gas, at rest or not, that is to say at zero flow rate or not, its temperature is stabilized at a given temperature (T) and the voltage at the terminals of the hot wire or of a resistance placed in series with the hot wire is then established at a given value (V).

In a conventional, but not obligatory manner, if it is desired to work with a hot wire kept at a constant temperature, the current being controlled so as to obtain this characteristic, a choice is made to carry out a voltage measurement (V) at the terminals of a resistance placed in series with said hot wire. In the case where it is desired to work with a constant current, the choice is made to carry out voltage measurements (V) at the terminals of the hot wire.

Thus, when this metal wire, still traversed by the current (I), is placed in a flow (D) of anaesthetic gas lacking xenon, the voltage at the terminals of the metal wire or of the resistance placed in series with said wire varies as a function $f_0$ of the flow rate D according to the following formula:

$$V = f_{0\ O2\%, N2O\%, AA\%, CO2\%, HR, T_g^\circ}(D)$$

The function $f_0$ also depends on the volume content O2% of $O_2$ in the gas, the volume content $N_2O$ % of nitrous oxide, the content AA % of anaesthetic agent (halogenated for example), the content CO2% of carbon dioxide and the relative humidity HR of the gas, the gas measured being at a temperature Tg°.

The function $f_{0\ O2\%,N2O\%,HR,Tg°}$ may be obtained conventionally by piecewise linearization or by an approximation by the method of least squares from calibration points (on a test bench) as many as are necessary for obtaining the desired precision.

This function $f_0$ depends however only to a minor extent on the contents O2%, AA %, CO2% and N2O % and the relative humidity HR and the temperature Tg° of the gas.

Thus, by measuring the voltage V at the terminals of the metal wire or of the resistance placed in series with said wire traversed by the given electric current (I), it is possible to deduce therefrom the flow rate (D) of anaesthetic gas without xenon sweeping over the metal wire by the formula:

$$D = f_{0\ O2\%,N2O\%,AA\%,CO2\%,HR,Tg°}^{-1}(V)$$

In addition, when this metal wire, still traversed by the current (I), is placed in a flow of anaesthetic gas containing a non-zero proportion of xenon Xe %, the voltage at the terminals of the metal wire varies according to the following formula:

$$V = f_{Xe\%,O2\%,N2O\%,AA\%,CO2\%,HR,Tg°}(D)$$

The current (I) may be preadjusted in the factory or even adjusted by periodic calibration initiated by the user or the machine in order to center the voltage measurement (V) within a given working voltage range, it being possible for calibration to be carried out on a first reference gas (air or pure $O_2$) containing no xenon (0%) or even possibly on a second reference gas containing xenon in a significant quantity (from 50 to 100% for example).

Thus, as previously, by measuring the voltage (V) at the terminals of the metal wire traversed by the given current (I) or at the terminals of the resistance in series with the wire, it is possible to deduce the flow rate (D) of anesthetic gas with a xenon content Xe % in which the metal wire is situated, by using the formula:

$$D = f_{0\ Xe\%,O2\%,N2O\%,AA\%,CO2\%,HR,Tg°}^{-1}(V)$$

In a simple conventional manner, the hot-wire(s) sensor may be produced using a single metal wire placed for example perpendicular to the direction of flow of gas of which the xenon concentration is to be measured.

In a non-obligatory manner that is more sophisticated but more precise, the hot wire(s) sensor may be made using two metal wires, one placed perpendicular to the direction of the gas flow (wire 1 traversed by a current I1) and the second that is more or less in the axis of the same gas flow (wire 2 traversed by a current I2), the formulae enabling the voltage to be linked to the flow rate and to the various concentrations of xenon, CO2, O2, AA, N2O and HR being established as follows:

$$V = f_{0\ Xe\%,O2\%,N2O\%,AA\%,CO2\%,HR,Tg°}^{-1}(D) =$$
$$f1_{Xe\%,O2\%,N2O\%,AA\%,CO2\%,HR,Tg°}(D) -$$
$$f2_{Xe\%,O2\%,N2O\%,AA\%,CO2\%,HR,Tg°}(D)$$

and $$D = f_{Xe\%,O2\%,N2O\%,AA\%,CO2\%,HR,Tg°}^{-1}(V)$$

The principle for measuring the flow rate of an anaesthetic gas of which the composition is known (and in particular the xenon concentration) by means of a hot-wire(s) sensor having been described, the reasoning is reversed leading to the production by the measuring system of the xenon concentration etc. Knowing the flow rate or the flow rate measurement, the xenon concentration in the analyzed gas is deduced therefrom.

Thus, in a respiratory anesthesia apparatus, the measurement of the xenon flow rate may be carried out in the main flow or in the flow diverted from said main gas flow.

When the hot-wire(s) sensor (with a single metal wire or two metal wires) is placed in diverted gas flow drawn off from the main gas flow (cf. FIGS. 1 to 4 below), such as a known aspiration flow rate of anaesthetic gas (Dc) obtained for example by means of a suction pump, it is possible to deduce therefrom the inhaled and/or exhaled and/or mean and/or instantaneous xenon concentration Xe % from the voltage measurement V according to the following formula:

$$Xe\% = h_{DC,O2\%,N2O\%,AA\%,CO2\%,HR}(V) \text{ with}$$

$$V = f_{Xe\%,O2\%,N2O\%,AA\%,CO2\%,HR}(Dc) \quad (1)$$

a formula in which the function $h_{DC,O2\%,N2O\%,AA\%,CO22\%,HR}$ is found to be linear and may be obtained by calibration with a flow rate Dc of gas at a known concentration (pure xenon and/or pure $O_2$ and/or pure air).

Thus, for as many values of the aspiration flow rate Dc that are desired or necessary, a linear curve is memorized in the memory by means of the apparatus, that is a straight line of the type b+a×[Xe]=V where V is the voltage, [Xe] the xenon concentration and a and b are positive or negative coefficients corresponding to each value of the flow rate Dc, a and b being obtained by calibration with a flow rate Dc of gas at a known concentration (pure xenon and/or pure $O_2$ and/or pure air).

When used in operation, the calculating means then use values of the voltage (V) and the value of the flow rate (Dc) in order to determine a xenon concentration (Xe %) in the gas flow from the linear curve memorized in the memory means of the apparatus corresponding to the selected value for the flow rate Dc.

Advantageously, the curves are, for as many values of the aspiration flow rate (Dc) that are desired or are necessary, calibrated (with a flow rate established at the value (Dc) of the gas of which the xenon content is known, namely pure xenon and/or pure $O_2$ and/or pure air) before memorization, and/or are updated periodically and automatically during the use of the apparatus.

Figure 9A:
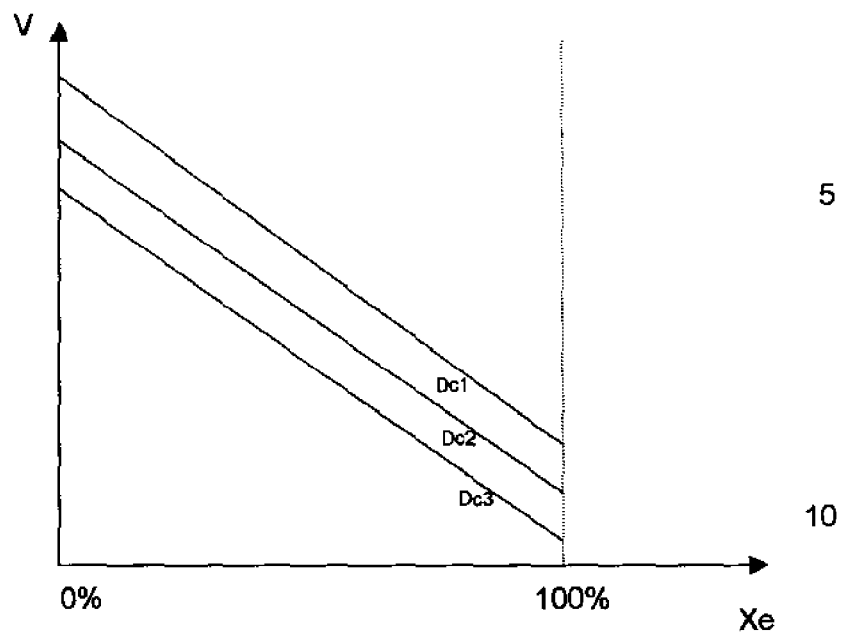
FIGS. 9a and 9b show an example of sets of curves (for 3 values of the flow rate Dc) showing the linearity existing between the xenon content (Xe %) and the voltage (V).
Figure 9B:
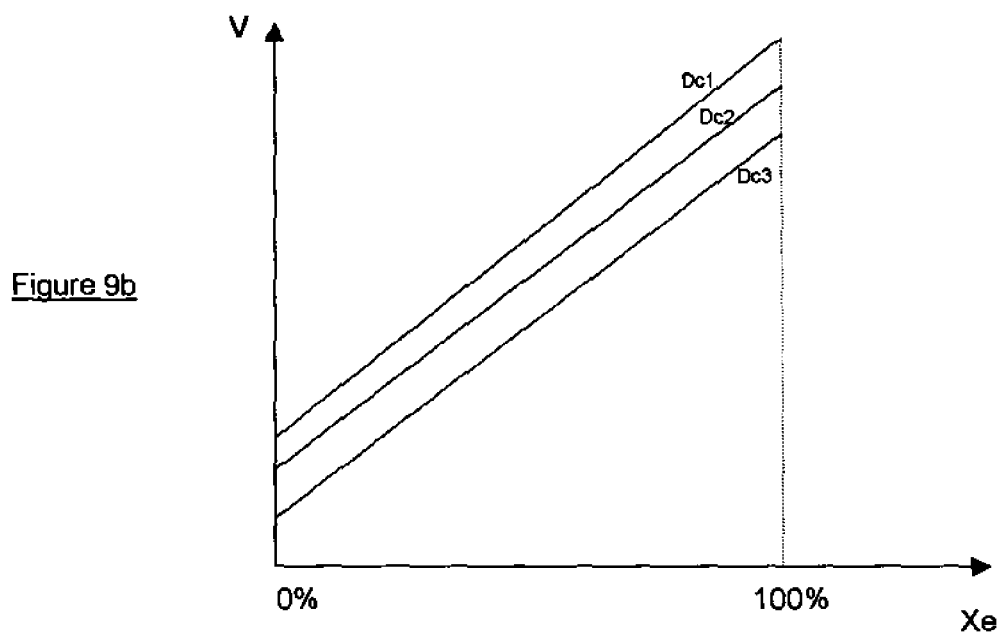

The appended FIGS. 9a and 9b represent an example of such sets of curves (for 3 values of the flow rate Dc) showing the linearity existing between the xenon content (Xe %) and the voltage (V).

Alternatively, when the sensor having a single hot wire or two wires is placed directly in the flow of anesthetic gas inhaled by the patient and/or exhaled by him or her, that is to say the main gas flow (cf. FIGS. 5 to 8), provided that the measurement is available of said main flow rate (Dp) of gas inhaled and/or exhaled, for example obtained in a prescribed manner by the system for monitoring the inhaled and exhaled patient gas flow rates, it is possible to deduce the inhaled and/or exhaled and/or mean and/or instantaneous xenon concentration Xe % from the voltage measurement V according to the following formula:

$$Xe\% = h_{Dp,O2\%,N2O\%,AA\%,CO2\%,HR,Tg°}(V)$$

$$\text{with } V = f_{Xe\%,O2\%,N2O\%,AA\%,CO2\%,HR,Tg°}(Dp) \quad (2)$$

a formula in which the function $h_{Dp,O2\%,N2O\%,AA\%,CO2\%,HR,Tg°}$ is found to be linear and may be obtained by calibration with a flow rate Dp of gas at a known concentration (pure xenon and/or pure $O_2$ and/or pure air).

Thus, for as many values of the flow rate Dp that are desired or necessary, a linear curve is memorized in the memory means of the apparatus, that is a straight line of the type $b+a \times [Xe]=V$ where V is the voltage, [Xe] the xenon content and a and b are positive or negative coefficients corresponding to each given flow rate value, a and b being obtained by calibration with a flow rate Dp of gas at a known concentration (pure xenon and/or pure $O_2$ and/or pure air).

When used in operation, the calculating means then use values of the voltage (V) and the value of the flow rate (Dp) in order to determine a xenon concentration (Xe %) in the gas flow from the linear curve memorized in the memory means of the apparatus corresponding to the selected value for the flow rate Dp.

Advantageously, the curves are, for as many values or the aspiration flow rate (Dp) that are desired or are necessary, calibrated (with a flow rate established at the value (Dp) of the gas of which the xenon content is known, namely pure xenon and/or pure $O_2$ and/or pure air) before memorization and/or are updated periodically and automatically during the use of the apparatus.

Figure 9C:
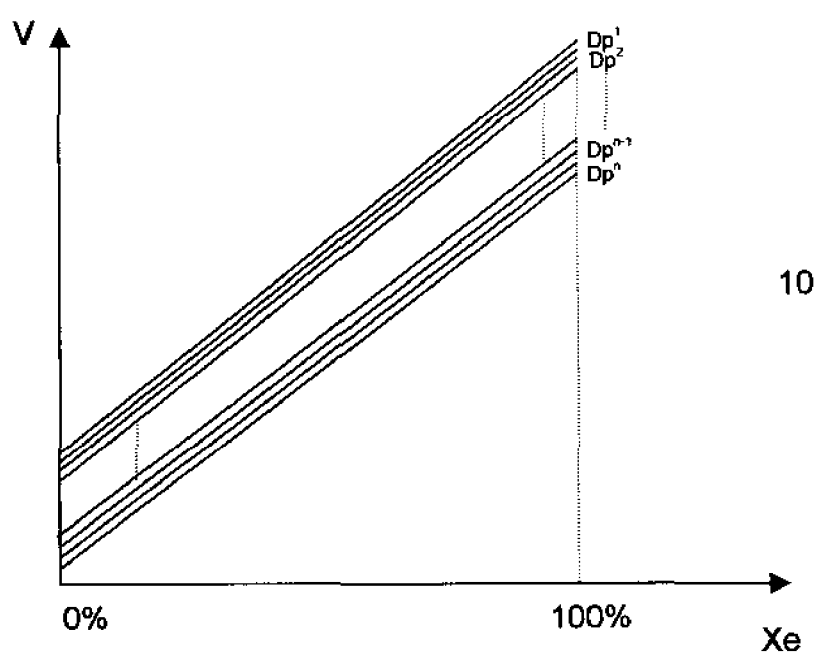
FIGS. 9c and 9d show an example of a set of curves (for as many values of the flow rate Dp that are desired or necessary) showing the linearity existing between the xenon content (Xe %) and the voltage (V).
Figure 9D:
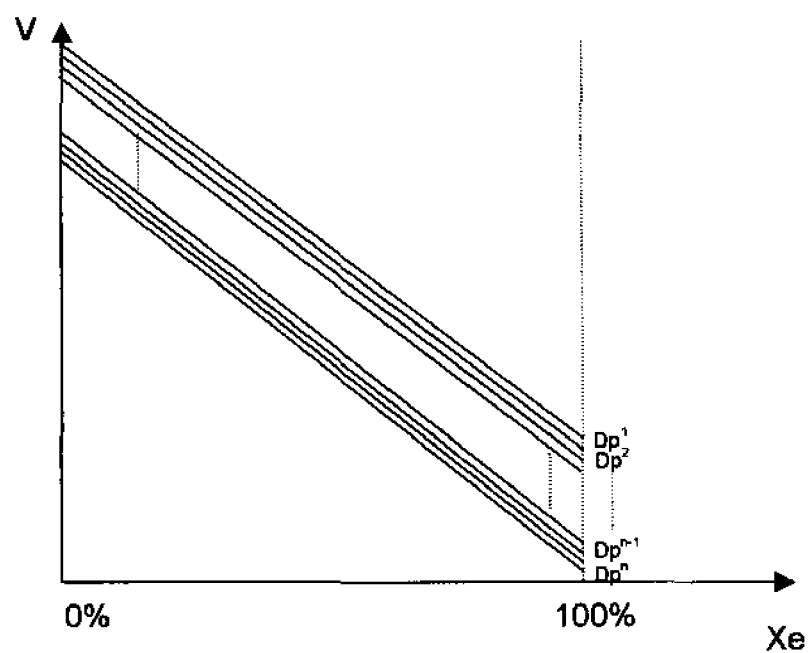

The appended FIGS. 9c and 9d show an example of such a set of curves (for as many values of the flow rate Dp that are desired or necessary) showing the linearity existing between the xenon content (Xe %) and the voltage (V).

In all cases, if it is desired to obtain the xenon content (Xe %) with no great precision, dependence on the O2% and/or AA % and/or N2O % concentrations and/or relative humidity HR of the gas will be ignored. If on the other hand it is desired to obtain the xenon content (Xe %) with greater precision, these parameters will be taken into account. Nevertheless, it should be noted that these formulae (1) and (2) are dependent only to a slight extent on the O2 and N2O contents and on the relative humidity HR of the gas, they being even less dependent on the CO2 and AA contents.

For a further understanding of the nature and objects for the present invention, reference should be made to the detailed description, taken in conjunction with the accompanying figures, in which like elements are given the same or analogous reference numbers and wherein:

FIG. 1 illustrates the first embodiment of an anesthesia apparatus according to the invention including the real-time measurement of the flow rate of xenon in a diverted gas flow by using a hot-wire(s) sensor so as to deduce therefrom the instantaneous and/or mean xenon concentrations in the main circuit, as well as means for the real-time measurement of the flow rate of gas inhaled by the patient and exhaled by him or her in the main circuit, also called the "patient circuit".

The apparatus or ventilator of FIG. 1 comprises an inlet unit 1 having connecting means to which the xenon source and other gas sources supplying the anesthesia apparatus are connected, such as gas bottles or a wall system, in particular for air (AIR) oxygen ($O_2$) and/or nitrous oxide ($N_2O$) sources.

This unit 1 is in fluidic communication with the inlet to a mixer 2 where xenon is mixed with the other gas or gases that are intended to form the anesthetic gas mixture, in particular oxygen in sufficient quantity for the patient (non-hypoxic).

The outlet from the mixer 2 supplies a vessel 14 for halogenated compounds with the gaseous mixture mounted on a vessel support 13, containing a halogenated compound, such as Sevoflurane, Isoflurane or Desflurane (most commonly employed) Halothane or Enflurane (less used), designed to be carried by the flow of anaesthetic gas to the patient 15.

The halogenated gas mixture leaving the vessel 14 is introduced into a main circuit or patient circuit having an inhalation branch 16 for leading said mixture to the patient 15 and an exhalation branch 18 for recovering all or part of the gas exhaled (loaded with $CO_2$) by the patient 15. The inhalation 16 and exhalation 18 branches form a circuit in a loop or closed circuit.

The connection between the inhalation 16 and exhalation 18 branches and the patient 15 is made via, for example, a Y-piece 17 and a respiratory mask, a tracheal tube or the like.

Inhalation 7 and exhalation 8 non-return valves are preferably provided respectively on said inhalation 16 and exhalation 18 branches.

The exhalation branch 18 has a device 9 for absorbing $CO_2$ comprising a vessel filled with an absorbent material, such as lime, making it possible to remove $CO_2$ exhaled by the patient 15 and conveyed by the exhaled gas in the exhalation branch 18 of the main circuit, as well as an exhaust valve 10 making it possible to evacuate any gaseous surplus and/or any excess gas pressure in the exhalation branch 18.

In addition, the ventilator of the invention includes, in a known manner, a mechanical ventilation bellows 4a incorporated in a chamber 4b, as well as a manual ventilation balloon 5, which may be selectively connected fluidically to the main circuit CP in order to supply gas under pressure via a bellows/balloon selector 6.

In the example, the main circuit CP alternatively called the "patient circuit" consists of an assembly of elements that have just been mentioned, namely: elements 4a, 4b, 5 to 12 and 16 to 18.

The control means 3 comprise, for example, at least one electronic control card and one or more on-board pieces of software or computer programs that make it possible to collect at least part of the information or signals coming from all or part of the sensors of the apparatus and process them and/or to carry out any necessary calculations for following the gas concentrations and/or for controlling the various elements of the apparatus.

In particular, a sensor 11 for the inhalation gas flow and a sensor 12 for the exhalation gas flow, provided respectively on the inhalation 16 and exhalation 18 branches of the main circuit (CP), measure the inhalation and exhalation flow rates in said branches and transmit the measurement signals thus obtained to the control means 3 by suitable electrical connections. In this way, the control means 3 are able to control the bellows 4 and/or the opening of the exhaust valve 10 and/or the inlet for suitable gases in the inlet unit 1 to which said control means are connected, via dedicated electrical connections, as may be seen in FIG. 1.

In order to be able to carry out a measurement and to follow effectively the xenon content of the gas mixture, the apparatus of the invention incorporates a gas analyzer module S6 called a "gas bench" including a hot-wire(s) sensor swept by a diverted flow of anaesthetic gas.

The gas analyzer module S6 is shown for a second time in an enlarged and detailed manner in FIG. 1 (cf. at the end of the curved arrow).

More precisely, as may be seen in FIG. 1, part of the gas flow based on xenon conveyed by the main gas circuit CP is drawn off at the Y-piece 17, via a sampling line that communicates fluidically with said main circuit CP.

The line S1 conveys anesthetic gas to a module S6 while previously causing it to pass through a water trap S1, where water vapor contained therein is removed before being conveyed, via a transfer line S3, to the module S6.

As regards the gas analyzer module S6, this includes, arranged on the gas flow passage:
    a suction pump S6-A (for example of the type of that fitted to gas benches BGA4800 or BGA4700 from the Andros company or the AION from the Artema company) for creating a known flow of anesthetic aspiration gas (Dc), a hot-wire sensor S6-E, consisting for example of a single platinum wire, traversed by an electric current of given intensity (I), for example an intensity of approximately 100 mA, with a measurement of the voltage (V) at the terminals of said wire when this is in contact with the flow containing xenon, an infrared cell S6-B (for example of the type of that fitted to gas benches BGA4800 or BGA4700 from the Andros company or the AION from the Artema company) making it possible to measure the instantaneous and/or mean and/or inhaled and/or exhaled concentrations of $CO_2$, $N_2O$, halogenated compounds, ethanol or any other gas that may be measured by this infrared technology, an $O_2$ paramagnetic cell or a chemical S6-C cell (for example of the type of that fitted to gas benches BGA4800 or BGA4700 from the Andros company or the AION from the Artema company according to options) in order to measure the instantaneous and/or mean and/or inhaled and/or exhaled concentrations of $O_2$, control means S6-D with software integrated on an electronic control card (of the type of that fitted to gas benches BGA4800 or BGA4700 from the Andros company or the AION from the Artema company), suitable connections connecting the infrared cell S6-B and the oxygen cell S6-C to the control means S6-D.

The outlet from the suction pump S6-A of the module S6 is connected to the exhalation branch of the main circuit, via a reinjection line S4, so as to reconvey thereto gas that has been withdrawn through the sampling line S1.

In addition, as shown, the measurement signals obtained with the hot-wire(s) sensor S6-E are transmitted to the control means S6-D via a suitable connection S6-F, said control means S6-D being themselves connected, via a suitable electrical connection S5, to the control means 3.

Calculations, in particular the xenon concentrations of the anesthetic gas, are performed by the control means S6-D of the module S6.

The gas analyzer module S6 is for example of the BGA4800, BGA4700 or BGA4900 type from the Andros company or AION from the Artema company to which has been added in particular hot-wire(s) sensor means such as for example a hot-wire sensor from the Taema company.

This gas analyzer module S6 thus makes it possible to perform on the gas aspirated through the sampling line S1 at a continuous flow rate, preferably adjustable to few tens or hundreds of mL/min, at least:

a real-time measurement of $O_2$, AA (halogenated compound present, of which the nature will be automatically detected or selected by the user according to the type of gas bench used), $N_2O$, $CO_2$, so as to obtain the corresponding contents or concentrations: $O_2\%$, $CO_2\%$, AA % and $N_2O$ %, a measurement of the fractions inhaled by the patient for these same gases so as to obtain values for the corresponding fractions inhaled: $FiO_2$, in $CO_2$, FiAA and $FiN_2O$, and a measurement of the fraction exhaled by the patient for these same gases so as to obtain values for the corresponding fractions exhaled: $FeO_2$, $etCO_2$, FeAA and $FeN_2O$.

It should be noted that although the hot-wire(s) sensor S6-E is shown at the inlet to the module S6 and upstream to the cell S6-C, it may also be inserted elsewhere, in particular downstream from the suction pump S6-A and/or upstream to and/or on the reinjection line S4, the latter being connected or not to the main circuit.

The hot-wire(s) sensor S6-E carries out, in real time, a measurement of the voltage (V) at the terminals of the hot wire, generated by the aspirated gas, and transmits it through the connection S6-F, with a more or less short known delay of a few tens or even a few hundreds of ms according to the regulated aspirated flow rate, to the control software S6-D of the anaesthetic gas analyzer so that this can deduce, via the formula (1) above, in particular:

a real-time measurement of the xenon content (Xe %) using the control value of the aspiration flow rate of the anesthetic gas analyzer S6 and a real-time measurement of the voltage of the hot wire, possibly compensated for by real-time measurements of the concentration $O_2\%$, $CO_2\%$, AA, $N_2O$ % and/or a measurement of the inhaled fraction in xenon (FiXe) using the real-time measurement of xenon content (Xe %) at the moment of inhalation, the calculating window and determination of FiXe being phased on that of the calculation and determination of the measurement in $CO_2$, and secondarily FiO2, FiAA and FiN2O and/or a measurement of the exhaled fraction in xenon (FeXe) using the real-time measurement of xenon content (Xe %) at the moment of exhalation, the calculating window and determination of FeXe being phased on that of the calculation and determination of the measurement etCO2, and secondarily FeO2, FeAA and FeN2O.

Alternatively, the gas analyzer module may be used to carry out a mean measurement of xenon concentration using the real-time measurement of (Xe %) obtained by using the control value of the aspiration flow rate of the anesthesia gas analyzer S6 and the mean value of the voltage measurement (V) of the hot wire calculated from the real-time measurement of the voltage of the hot wire, possibly compensated for by measurements of the mean concentrations $O_2\%$, $CO_2\%$, AA, $N_2O$ %, themselves calculated from real-time measurements $O_2\%$, $CO_2\%$, AA, $N_2O$ %, and this with the aid of formula (1).

In order to guarantee increased safety in use, the main circuit is duplicated with an auxiliary circuit 26 connected to the line 27 leading in gas containing xenon that itself supplies the main circuit.

The auxiliary circuit 26 is used in the case where the main circuit ceases to operate or malfunctions.

The auxiliary circuit 26 comprises a manual insufflator 28 connected fluidically to said auxiliary circuit 26 that can be acted manually by the user, namely nursing personnel so as to send the anaesthetic gas to the patient 15. A patient interface is arranged downstream from the auxiliary circuit 26, such as a respiratory mask or a tracheal tube, supplying the upper airways of said patient 15 with anaesthetic gas, when the doctor or similar person operates the insufflator 28, that classically comprises a balloon and an inhalation and exhalation valve.

According to the invention, the bypass line S1 may be connected fluidically to the auxiliary circuit 26 in a site 30 situated between the insufflator 28 and the patient 15 as shown by the line 29, via suitable connecting means, for example a connection or filter or mask fitted with a port for connecting the sampling line, for example, a connector of the Luer type.

In this case, the xenon concentration is followed in the auxiliary circuit 26 and no longer in the main circuit CP.

The auxiliary circuit 26 is advantageously provided in various embodiments of the invention shown in FIGS. 1 to 8.

Figure 2:
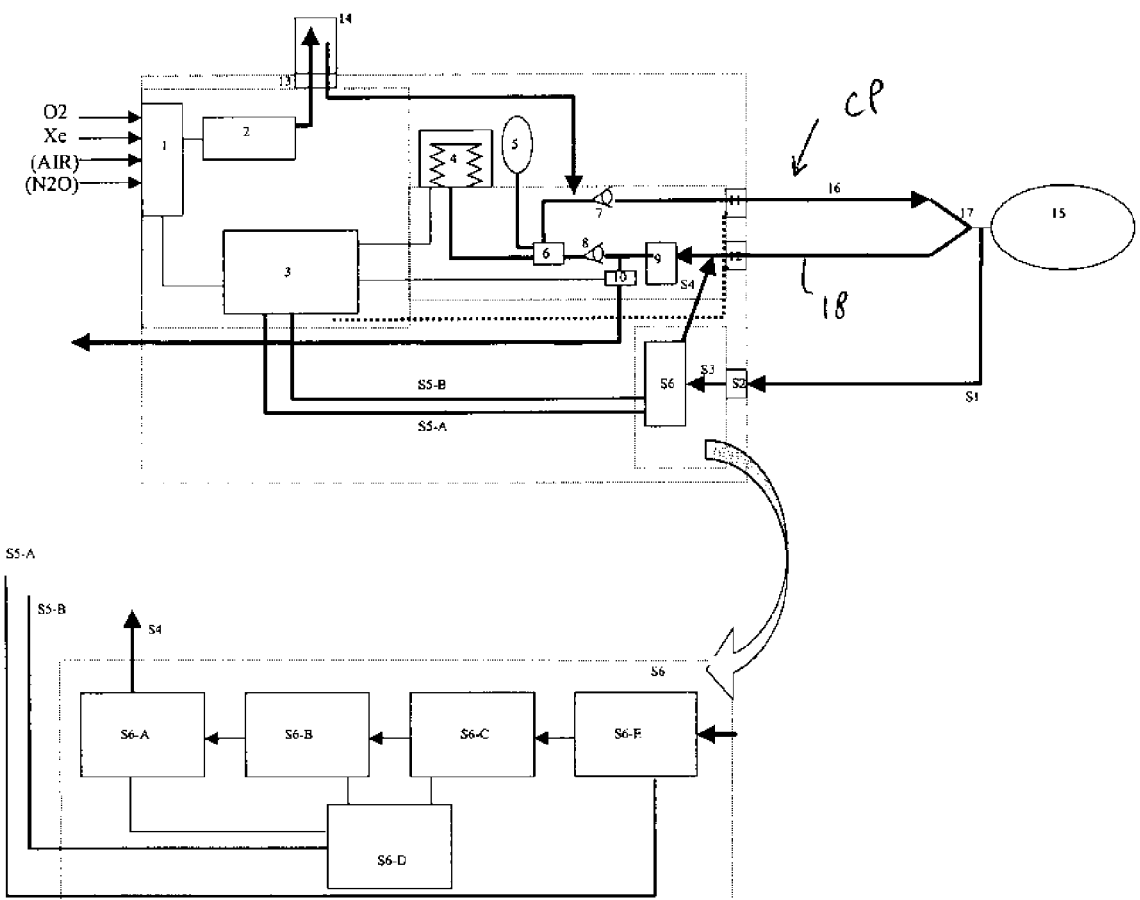
FIG. 2 shows a first variant of the embodiment of the apparatus of FIG. 1.
Figure 3:
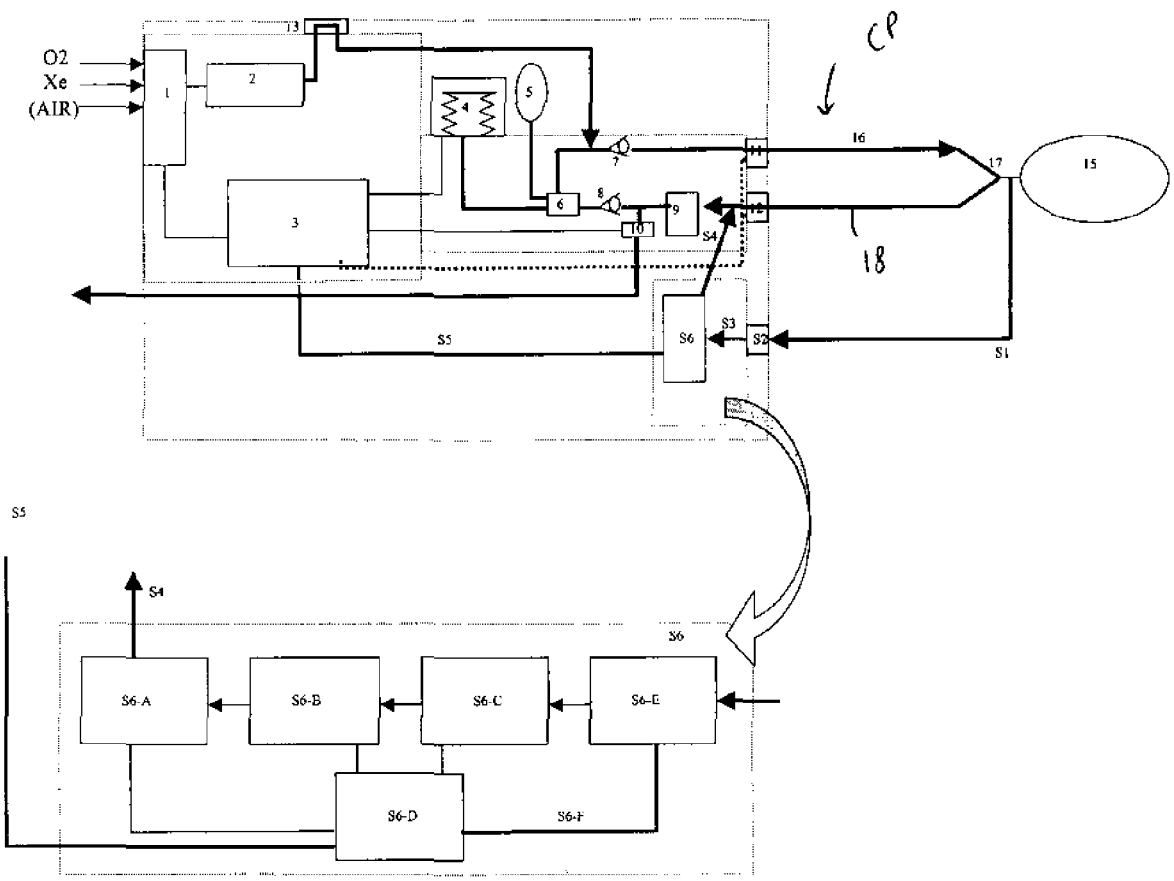
FIGS. 3 and 4 show respectively a second and third variant of the embodiment of the apparatus of FIG. 1 that may be used for anesthesia only under xenon, without the use of halogenated compounds.
Figure 4:
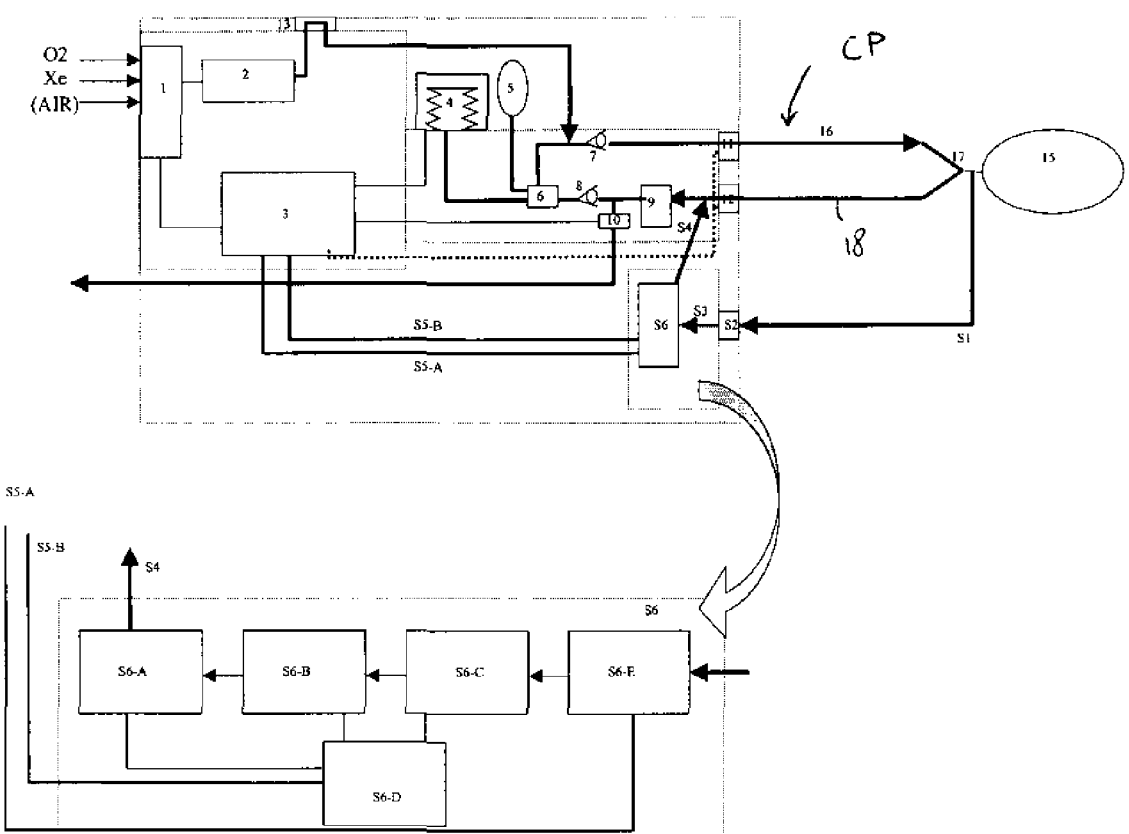

In the embodiments of FIGS. 2 to 4, identical elements to those described above for FIG. 1 are denoted by the same references and are not described in detail a second time.

FIG. 2 shows a first variant of the embodiment of the apparatus of FIG. 1 according to which the measuring signals coming from the hot-wire(s) sensor S6-E are transmitted, in this case, to the control means 3 via a specific direct link S5-A. Calculations in particular of xenon concentrations of the anaesthetic gas are carried out in the control means, as previously detailed. In addition, in this case, the control means S6-D are also connected via a suitable electrical connection S5-B, to the control means 3. The xenon concentration is thus followed by the means 3 for controlling the ventilator and not by the module S6.

FIG. 3 shows a second variant of the embodiment of the apparatus of FIG. 1 that can be used for producing anesthesia only under xenon, without the use of halogenated compounds.

In this case, measurements carried out by the module S6 are identical to measurements carried out in the case of FIG. 1, with the exception of those concerning the halogenated compounds, which are no longer carried out on account of the fact that the vessel 14 for halogenated compounds and the vessel support 13 are dispensed with. In point of fact, as will be seen in FIG. 3, the gas flow coming from the mixer 2 is directly conveyed (without being charged with halogenated compounds, in the absence of a vessel) toward the main circuit.

Such an apparatus may be useful when it is necessary for example to couple inhalatory anesthesia with xenon with anesthesia of the intravenous type or the like since, in such a medical situation, anesthesia by halogenated products is not required on account of the use of intravenous products.

FIG. 4 shows a third variant of the embodiment of the apparatus of FIG. 1. This variant can also be used for producing anesthesia only under xenon, without the use of halogenated compounds, based on a combination of the embodiments in FIGS. 2 and 3. More precisely, the apparatus of FIG. 4 may be distinguished from that of FIG. 2, solely in that it does not include the vessel for halogenated compounds.

The embodiments of FIGS. 1 to 4 are particularly preferred in embodiments of the invention.

Figure 5:
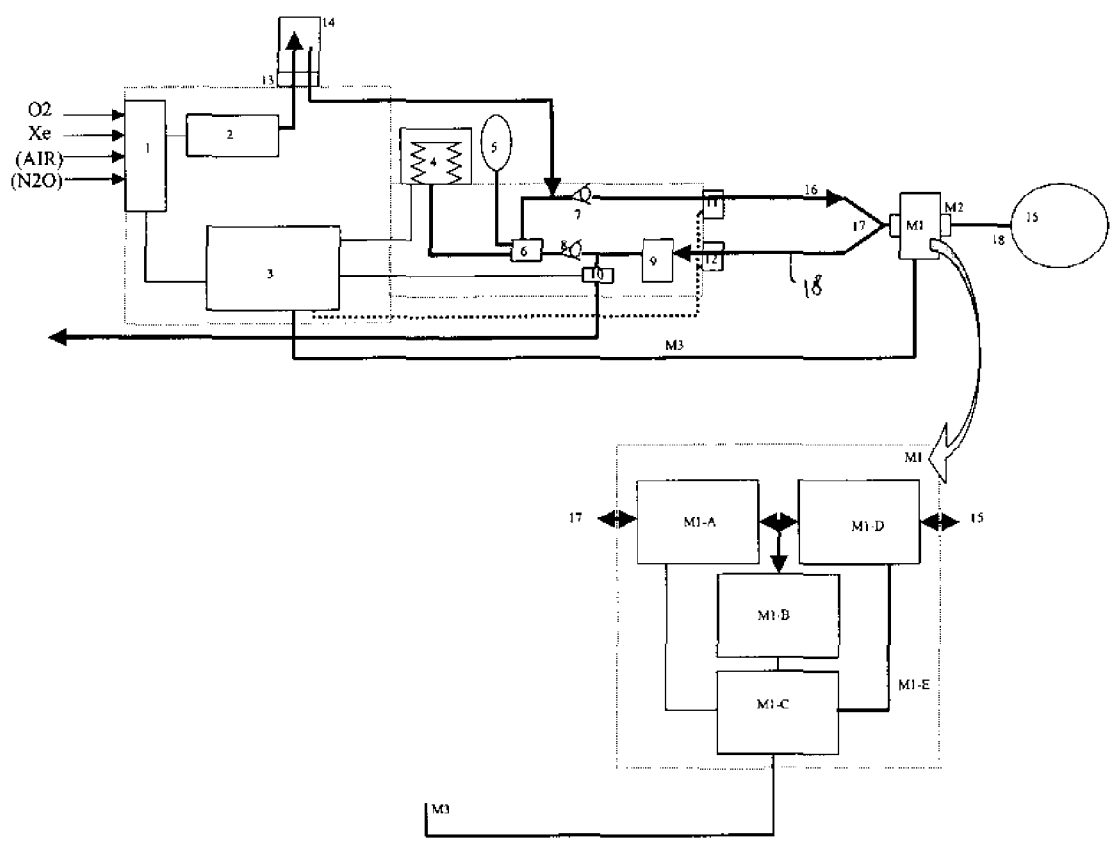
FIG. 5 shows a second embodiment of an apparatus according to the invention that may be used for anesthesia under xenon with the possible use of halogenated compounds and with a hot wire or wires placed in the main gas flow.

FIG. 5 illustrates a second embodiment of an anesthesia apparatus according to the invention including means for measuring, in real time, the xenon flow rate in the main gas flow by means, as previously, of the use of a hot-wire(s) sensor so as to deduce therefrom, for example, the instantaneous and/or mean xenon concentrations in the main circuit CP, as well as means for measuring, in real time, the flow rate of gas inhaled by the patient and exhaled by him or her into the main circuit.

As may be seen in FIG. 5, the ventilation apparatus comprises the same elements as those of FIG. 1, with the exception of the module S6 which has been removed and replaced, in this case, by another gas analyzer module M1, that is positioned directly on the main gas circuit. In particular, the gas analyzer module M1 is inserted into the patient connection means, such as a patient adapter M2, itself connected onto the Y-piece 17 at the end of the main circuit. In this way, the analyzer module M1 may carry out, on the gas inhaled by the patient and then exhaled by him or her, at least the same measurements as in the case of FIG. 1.

The module M1 that can be used to this end is for example the anesthesia gas analyzer IRMA OR or OR+ available (with its corresponding patient adapter M2) from the Phase In company and to which a hot-wire(s) sensor has in particular been added.

The module M1 is shown a second time in an enlarged and detailed manner in FIG. 5 (cf. at the end of the curved arrow).

More precisely, this module M1 receives from the software driving the control means 3 of the ventilator, with a known more or less short delay of several tens to several hundreds of milliseconds (ms), the real-time measurement of the inhaled and exhaled gas flow rate, this gas flow rate being measured by flow sensors 11 and 12 as explained above.

In addition, the anesthetic gas coming from the Y-piece 17 enters the module M1 while passing through a hot wire(s) sensor M1-D, arranged in series, between an infrared cell M1-A and an intubation tube 18 in order to produce, in real time, the voltage measurement (V) at the terminals of the hot wire, generated by the inhaled and exhaled gases, as previously, and that transmits it by a connection M1-E, with a more or less short known delay of several tens to several hundred ms to the calculating software of the control means M1-C of the analyzer M1. As a variant, the hot-wire(s) sensor M1-D is arranged between the Y-piece 17 and the infrared cell M1-A.

An $O_2$ cell M1-B of the module M1 makes it possible to measure the oxygen content.

Information on flow rates is conveyed by the control means 3 of the ventilator to the control means M1-C of the module M1 via a connection M3.

In addition, the control means M1-C of the module M1 are themselves connected to the $O_2$ cell M1-B, to the hot-wire(s) sensor M1-D via the connection M1-E, and to the infrared cell M1-A.

By applying the formula (2) above, the control means M1-C may deduce the same concentrations therefrom, in particular that of xenon, and other information described in the case of FIG. 1.

It is of course possible, as previously (FIG. 1), equally to carry out a measurement of the mean xenon concentration Xe % using the real-time measurement Xe % obtained in this way, the latter being obtained by using the real-time measurement of the inhaled and exhaled gas flow rate as well as the real-time measurement of the voltage of the hot wire, possibly compensated for by measurement of mean concentrations O2%, CO2%, AA % and N20% as previously explained.

Figure 6:
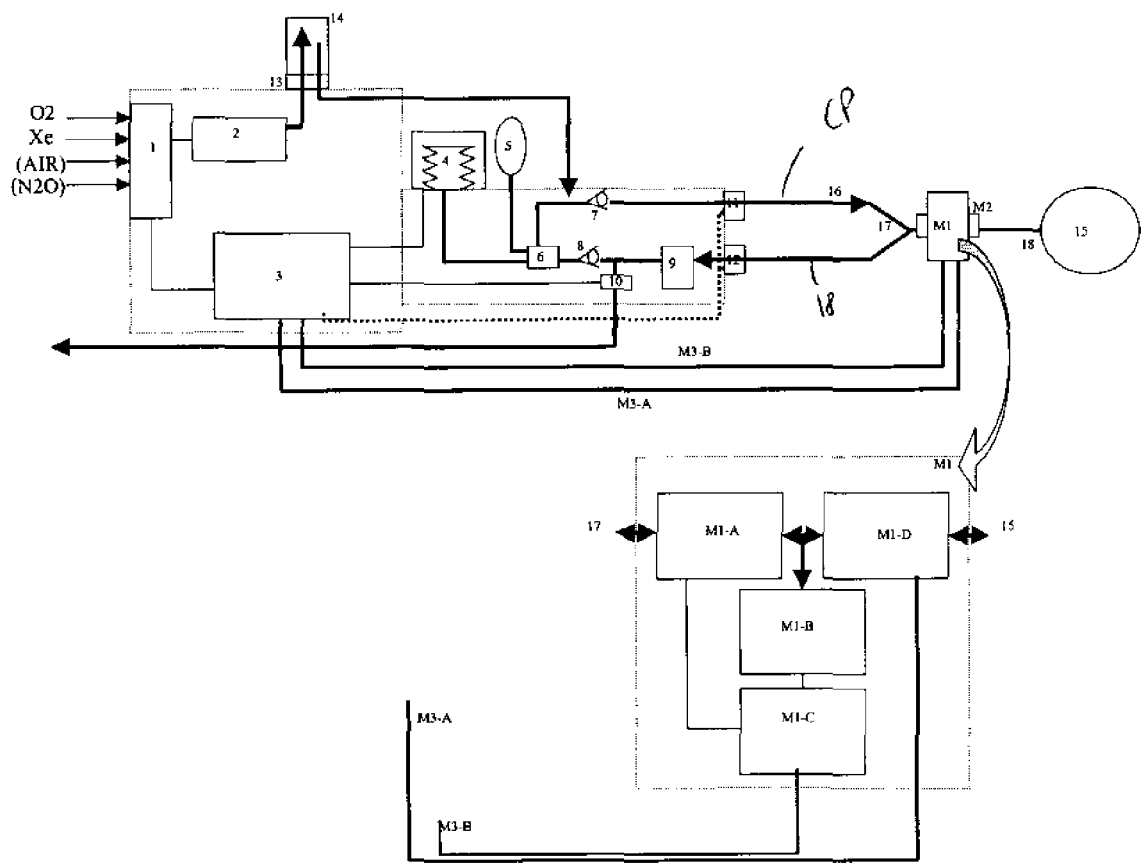
FIG. 6 shows a first variant of the embodiment of the apparatus of FIG. 5.
Figure 7:
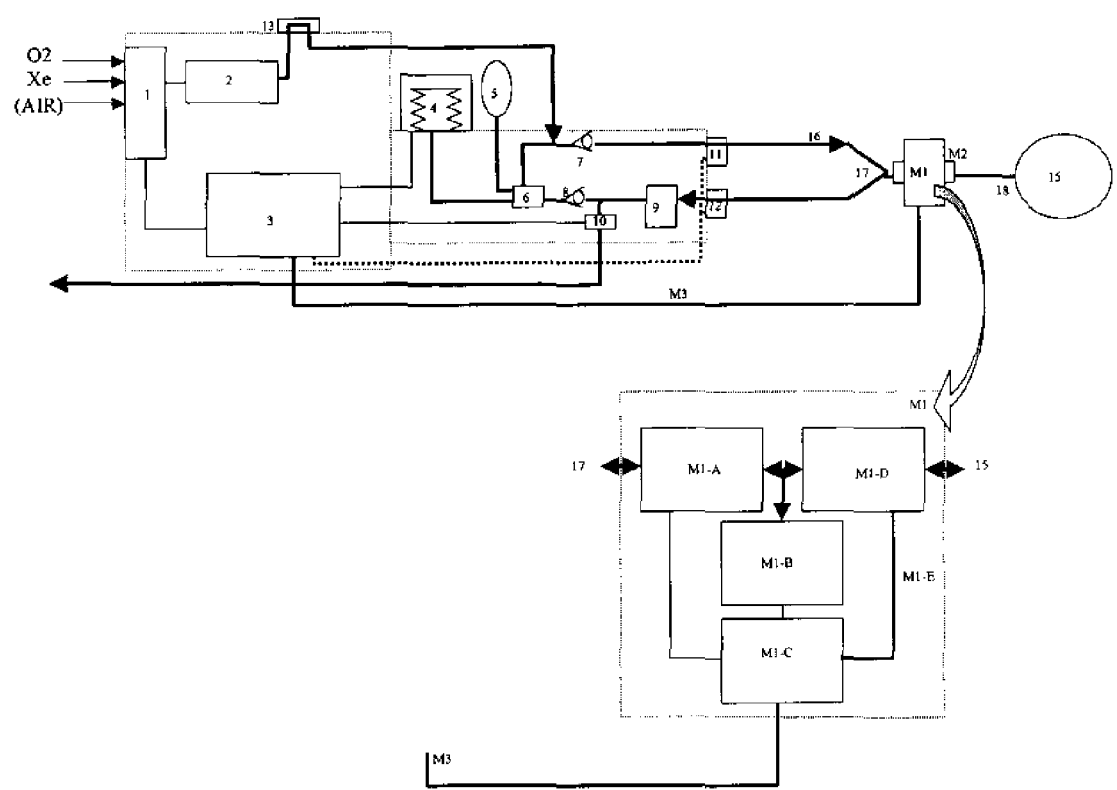
FIGS. 7 and 8 show respectively a second and third variant of the embodiment of the apparatus of FIG. 5 that may be used for anesthesia only under xenon, without the use of halogenated compounds.
Figure 8:
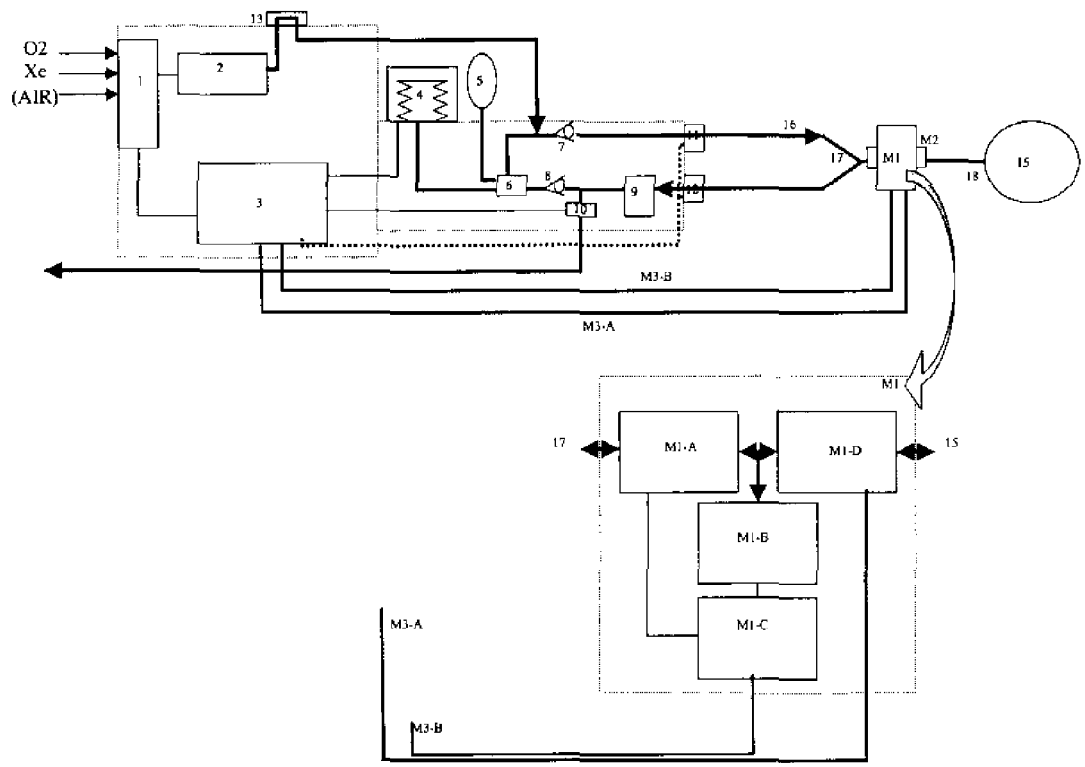

In the embodiments of FIGS. 6 to 8, elements identical to those described above for FIG. 5 are denoted by the same references and are not described in detail a second time.

FIG. 6 shows a first variant of the embodiment of the apparatus of FIG. 5, in which monitoring of the mean xenon concentration is carried out by the control means 3 of the ventilator and no longer in the module M1.

To this end, the measurement signals coming from the hot wire(s) sensor M1-D are transmitted by the connection M3-A to the control software of the control means 3 of the ventilator. The control means 3 of the ventilator may thus deduce therefrom a measurement of the mean xenon concentration Xe % using the real-time measurement Xe %, as previously with the aid of formula (2) above.

As regards the control means M1-C of the module M1, these are connected to the control means 3 of the ventilator by means of a dedicated line M3-B.

FIGS. 7 and 8 show respectively variants of the apparatus of FIG. 5 and FIG. 6, that can be used for anesthesia only under xenon, without the use of halogenated compounds, variants for which the vessel 14 for halogenated compounds and the vessel support 13 have been dispensed with (as in the embodiments of FIGS. 3 and 4 above).

In the case of FIG. 7, monitoring of the inhaled/exhaled concentrations of xenon is carried out in and via the module M1, as in the case of FIG. 5, whereas in the case of FIG. 8, it is carried out in the ventilator by the control means 3, as for FIG. 6.

The apparatus of the invention can be used in any circumstance and in any place, in particular in an operating unit, during anesthesia phases with xenon, so as to improve the safety of patients and comes within the scope of the obligations to monitor anesthetizing gases. In such a gas, gaseous xenon is always mixed with oxygen alone, air or then with oxygen and possibly one or more halogenated compounds and/or with nitrous oxide.

The hot wire(s) sensor according to the invention may of course use one or more wires composed of any suitable electrically conducting material.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An apparatus for the respiratory anesthesia of a patient by administration of a gas containing gaseous xenon comprising:
    a main gas circuit (CP) in an open or closed circuit having an inhalation branch for leading a first gas mixture containing xenon to the patient and an exhalation branch for conveying a second gas mixture containing xenon exhaled by the patient;
    means for supplying gaseous xenon connected to the main circuit for supplying the inhalation branch of the main circuit with the first gas mixture containing xenon;
    means for determining the xenon concentration in order to determine the gaseous xenon content in at least part of the main circuit;
    wherein said means for determining the xenon concentration comprises:
    at least one hot-wire sensor having at least one electrically conducting wire, in direct contact with at least part of the first or second gas flow containing xenon; and
    calculating means cooperating with the hot-wire(s) sensor for determining the xenon concentration (Xe %) in said first or second gas flow containing xenon;
    means capable of and designed for generating an electric current in at least one hot wire of said at least one hot-wire sensor,
    means for measuring the voltage capable of measuring at least one voltage value (V) at a terminal of at least one hot wire of said at least one hot-wire sensor or at a terminal of at least one resistance arranged in series with the at least one hot wire of said at least one hot-wire sensor when said at least one hot wire is a) in contact with the first or second gas flow containing xenon and b) traversed by an electric current of intensity (I),
    and in that the calculating means cooperate with the means for measuring voltage so as to determine, from the voltage measurement (V) carried out by said voltage measuring means, the xenon concentration (Xe %) in said first or second gas flow containing xenon.

2. The apparatus of claim 1, wherein the apparatus includes adjustable means capable of and designed for generating an electric current in the hot wire or in each of the hot wires of said at least one hot-wire sensor, said means for generating a current being designed for, and being capable of controlling the intensity of the electric current passing through the hot wire or wires of said at least one hot-wire sensor, so that, whatever the composition of the gas passing over said at least one hot-wire sensor(s), the intensity of the current passing through the hot wire or wires is kept substantially constant and/or a temperature of the hot wire or wires of said at least one hot-wire(s) sensor is kept substantially constant.

3. The apparatus of claim 1, wherein the calculating means use at least one value of the voltage (V) transmitted by the voltage measuring means and at least one value of the flow rate of the first or second gas flow containing xenon in order to determine the xenon concentration (Xe %) in the first or second gas flow containing xenon.

4. The apparatus of claim 1, wherein said at least one hot-wire(s) sensor is arranged on a bypass line communicating fluidically with the main circuit (CP), the bypass line being connected to the main circuit (CP) on the inhalation branch and/or on the exhalation branch and/or in a site located in the immediate vicinity of the patient's mouth.

5. The apparatus of claim 4, wherein the bypass line is connected in the region of a connecting site between the inhalation branch and the exhalation branch of said main circuit (CP).

6. The apparatus of claim 5, wherein the bypass line is connected in the region of a connecting Y-piece or a bacteriological filter arranged on the main circuit (CP).

7. The apparatus of claim 4, wherein a means for controlling the gas flow rate of the first gas mixture containing xenon are arranged on the bypass line so as to obtain a known anaesthetic gas aspiration flow rate (Dc).

8. The apparatus of claim 7 wherein the known anesthetic gas aspiration flow rate is selected from a constant and/or stable flow rate.

9. The apparatus of claim 4, wherein a means for controlling the gas flow rate of the first gas mixture containing xenon makes it possible to provide a desired flow rate of said first gas mixture containing xenon conveyed by the bypass line and put into contact with at least one hot wire.

10. The apparatus of claim 9 wherein the flow rate of said first gas mixture containing xenon gas is constant and/or stable.

11. The apparatus of claim 4, wherein the means for controlling the gas flow rate first gas mixture containing xenon comprises a suction pump for aspirating gas, and the suction pump is preferably associated with electronics for controlling said suction pump that may be programmed to generate a desired, precise and stable aspiration flow rate at one or more predefined and known values.

12. The apparatus of claim 1, wherein said at least one hot-wire(s) sensor is arranged directly on the main circuit (CP), on the inhalation branch and/or the exhalation branch and/or at the junction between the inhalation and exhalation branches.

13. The apparatus of claim 1, wherein the apparatus includes means for measuring the inhalation flow rate (Dpi) and/or the exhalation flow rate (Dpe) and/or the main flow rate (Dp) at the junction between the inhalation and exhalation branches of the gas flow circulating in the main circuit (CP), and the means for measuring flow rate comprising an inhalation flow rate sensor and an exhalation flow rate sensor, arranged respectively on the inhalation and exhalation branches of the main circuit in order to measure the inhalation and exhalation flow rates in said branches and to transmit the measurement signals obtained in this way to the calculating means so as to determine the xenon concentration in the inhalation branch and/or the exhalation branch and/or at the junction between the inhalation and exhalation branches.

14. The apparatus of claim 1, wherein said at least one hot wire sensor has several wires having different orientations relative to the gas flow.

15. The apparatus of claim 14 wherein the one hot wires sensor has two hot wires.

16. The apparatus of claim 1, wherein the calculating means are incorporated in a gas analyzer module connected to the main circuit.

17. The apparatus of claim 1, wherein the calculating means are incorporated in a module controlling the ventilator.

18. The apparatus of claim 1, wherein the apparatus further comprises an auxiliary gas circuit having an auxiliary inhalation branch enabling a third gas containing xenon to be led to the patient by means of a manual insufflator, calculating means being designed and adapted so that the calculating means can be connected to said auxiliary gas circuit in order to determine therein the xenon content when the third gas containing xenon is administered to the patient via said auxiliary gas circuit.

19. The apparatus of claim 1, wherein the calculating means use a voltage values (V) and a flow rate value (D) for determining a xenon concentration (Xe %) in the first or second gas flow containing xenon from one or more linear curves memorized in a memory means of the apparatus.

20. The apparatus of claim 19, wherein the one or more linear curves memorized in the memory means are defined by the formula $a \times [Xe] + b = V$ where V is the voltage, [Xe] is the xenon concentration and a and b are positive or negative coefficients corresponding to a given gas flow rate D.

* * * * *